United States Patent
Golner et al.

(10) Patent No.: US 6,568,287 B2
(45) Date of Patent: May 27, 2003

(54) OIL SAMPLING SYSTEM AND METHOD FOR ELECTRICAL POWER DEVICES

(75) Inventors: Thomas M. Golner, Pewaukee, WI (US); Peter C. Michel, Muskego, WI (US)

(73) Assignee: Waukesha Electric Systems, Waukesha, WI (US)

( * ) Notice: Subject to any disclaimer, the term of this patent is extended or adjusted under 35 U.S.C. 154(b) by 0 days.

(21) Appl. No.: 09/750,273

(22) Filed: Dec. 29, 2000

(65) Prior Publication Data

US 2002/0083781 A1 Jul. 4, 2002

(51) Int. Cl.[7] .................................................. G01N 1/00
(52) U.S. Cl. .................................................. 73/863.71
(58) Field of Search ........................ 73/863.72, 863.73, 73/863.81, 863.85, 863.86, 863.71, 864.33, 864.34, 19.01, 19.1, 19.11

(56) References Cited

U.S. PATENT DOCUMENTS

| | | | |
|---|---|---|---|
| 2,711,882 A | * | 6/1955 | Narbutovskih ................ 336/57 |
| 4,058,373 A | * | 11/1977 | Kurz et al. ................... 73/19.1 |
| 4,712,434 A | * | 12/1987 | Herwig et al. ........... 73/863.71 |
| 5,251,495 A | * | 10/1993 | Kuhner .................... 73/863.71 |
| 5,594,182 A | * | 1/1997 | Jansen ..................... 73/863.71 |

FOREIGN PATENT DOCUMENTS

| | | | | |
|---|---|---|---|---|
| JP | 0027654 | * | 2/1980 | .................. 336/55 |
| JP | 402190741 | * | 7/1990 | ................ 73/19.01 |

* cited by examiner

*Primary Examiner*—Robert Raevis
(74) *Attorney, Agent, or Firm*—Baker & Hostetler, LLP

(57) ABSTRACT

An oil sampling system for an electrical power device in which the oil flows through the sampling device in a closed loop with the oil containing apparatus of the electrical power device. Oil is taken in from an active region near the top of the oil containing apparatus and returned to a lower region thereof. This assures that the oil sample is representative of the oil in the system. For the case of a power transformer, the oil flow is by cooling with gravity assistance. For the case of a pumped system, such as a load tap changer, the oil flow is forced. The sampling procedure begins with connecting the sampling device in the closed loop. Oil is then passed through the sampling device until bubble free. The sampling device is then removed for analysis. The procedure does not need a flush operation or a flush container.

27 Claims, 4 Drawing Sheets

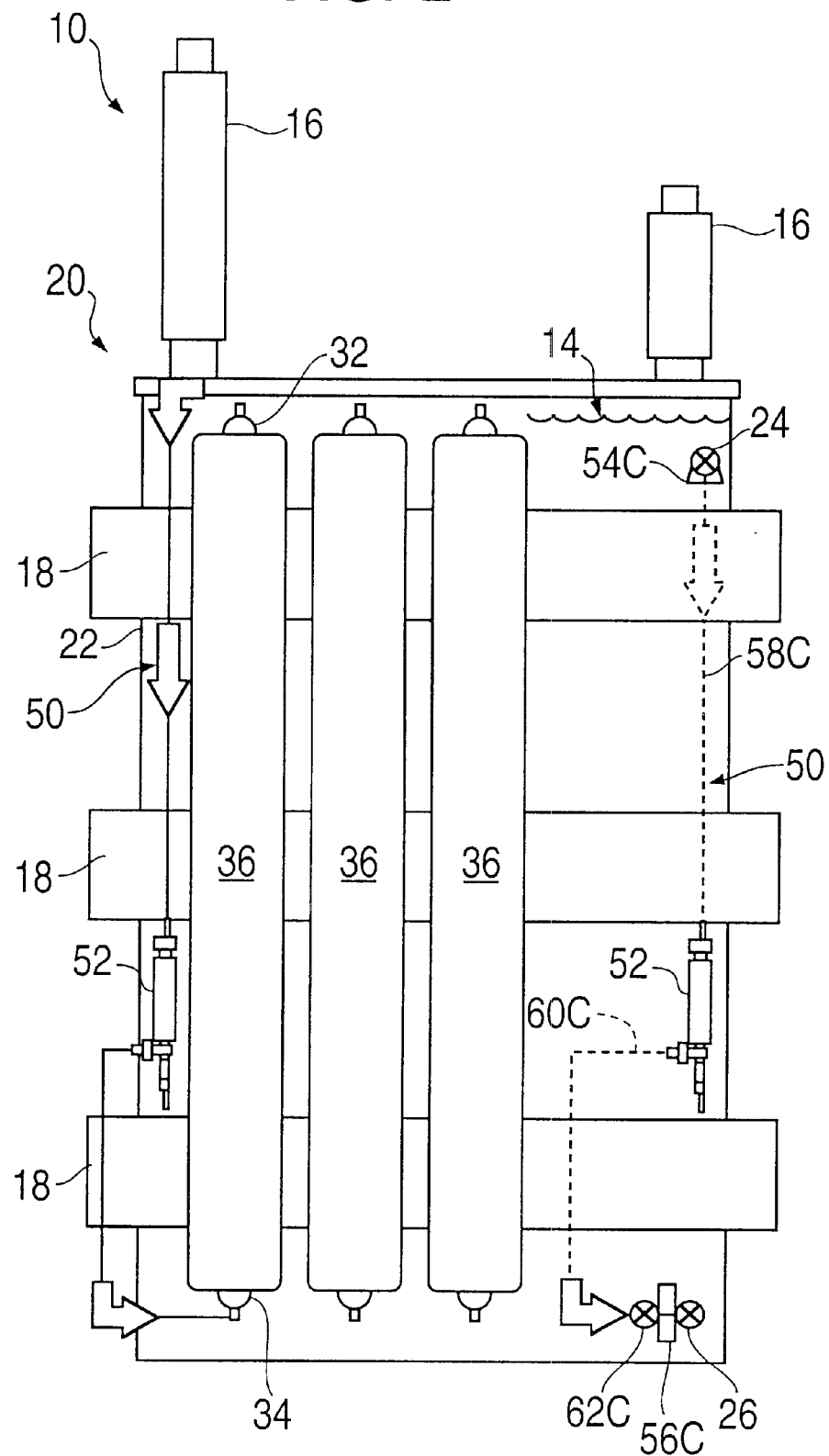

OIL SAMPLING SYSTEM AND METHOD FOR ELECTRICAL POWER DEVICES

FIELD OF THE INVENTION

This invention relates to a system and method for obtaining samples of oil from an oil system of an electrical power device, such as a power transformer, a load tap changer and the like.

BACKGROUND OF THE INVENTION

Active components of an electrical power device, such as a transformer, handle rather high electrical current that can cause arcing and/or over heating in an air environment. Oil systems have generally been employed to provide a relatively oxygen free environment and to cool the active components. A typical oil system contains a volume of oil and a tank in which the active component is submerged in oil. The tank generally includes a top fill valve and a bottom drain valve.

Abnormal operation of the power transformer can be detected by the analysis of gases and moisture contained in oil samples taken from the oil system at periodic intervals. This detection allows appropriate action to be taken that prevents serious damage to the power transformer. ASTM Designation: D 3613-92 describes a method for obtaining oil samples. This method obtains the sample from the bottom drain valve of the tank. This method has several drawbacks. The bottom drain valve is connected to the bottom of the tank, which is a dead zone or inactive region for the oil. Active regions for the oil are those in which the oil has contact with the active component and becomes heated. As the drain valve region is below the active component, the oil therein is not representative of the oil in the system. Sediment settles to the bottom region. For this reason, the method requires that the drain valve drain an initial volume of about two quarts of oil into a flush container to remove any effects of the sediment. Thereafter, the oil sampling device is connected with the drain valve and another quantity of about one quart of oil is passed through the sampling device into the flush container to assure a bubble free sample is obtained. The method requires that an oil flush container be used and that the flush oil be disposed of according to good environmental practice.

Thus, there is a need for an oil sampling system and method for obtaining a representative oil sample without handling a flush container and a disposition of flush oil.

SUMMARY OF THE INVENTION

The oil sampling system of the present invention provides the above mentioned need with a closed loop sampling of the oil of an electrical power device. An oil containing apparatus includes a tank in which a component of the electrical power device is submerged in oil. A sampling device is removably connected with first and second ports of the oil containing apparatus so that oil flows through the sampling device in a closed loop with the oil containing apparatus. The first port is located to receive a flow of oil from an active region of the oil containing apparatus.

In transformer embodiments, the second port is vertically displaced downwardly from the first port so that oil flows through the sampling device aided by cooling of the oil and gravity. In one embodiment, the first port is connected to a top fill valve of the tank and the second port is connected to a bottom drain valve of the tank. In other embodiments, the first port is connected to a top header pipe of a radiator of the oil containing apparatus. The second port is connected with a bottom header pipe of the radiator.

In another embodiment, a pump circulates the oil through the closed loop in which the sampling device is removably connected.

The method of the present invention begins with connecting the oil sampling device in the closed loop. The oil is passed through the sampling device. The sampling device is then disconnected with a quantity of oil for analysis. The oil is taken up from an upper active region of the oil containing apparatus so as to obtain a representative oil sample without the need for a flush container or flushing operation.

In one embodiment of the invention, a new sampling device is installed in the closed loop after an old sampling device is removed. This procedure assures that a sample is always available.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Other and further objects, advantages and features of the present invention will be understood by reference to the following specification in conjunction with the accompanying drawings, in which like reference characters denote like elements of structure and:

FIG. 2 is aside view of FIG. 1;

DETAILED DESCRIPTION OF THE PREFERRED EMBODIMENTS

It is contemplated that the oil sampling system and method of the present invention can be used with any electrical power device that requires an oil system for cooling and/or arcing prevention. By way of example, the oil sampling system and method of the invention are described herein for a power transformer and a load tap changer.

Figure 1:
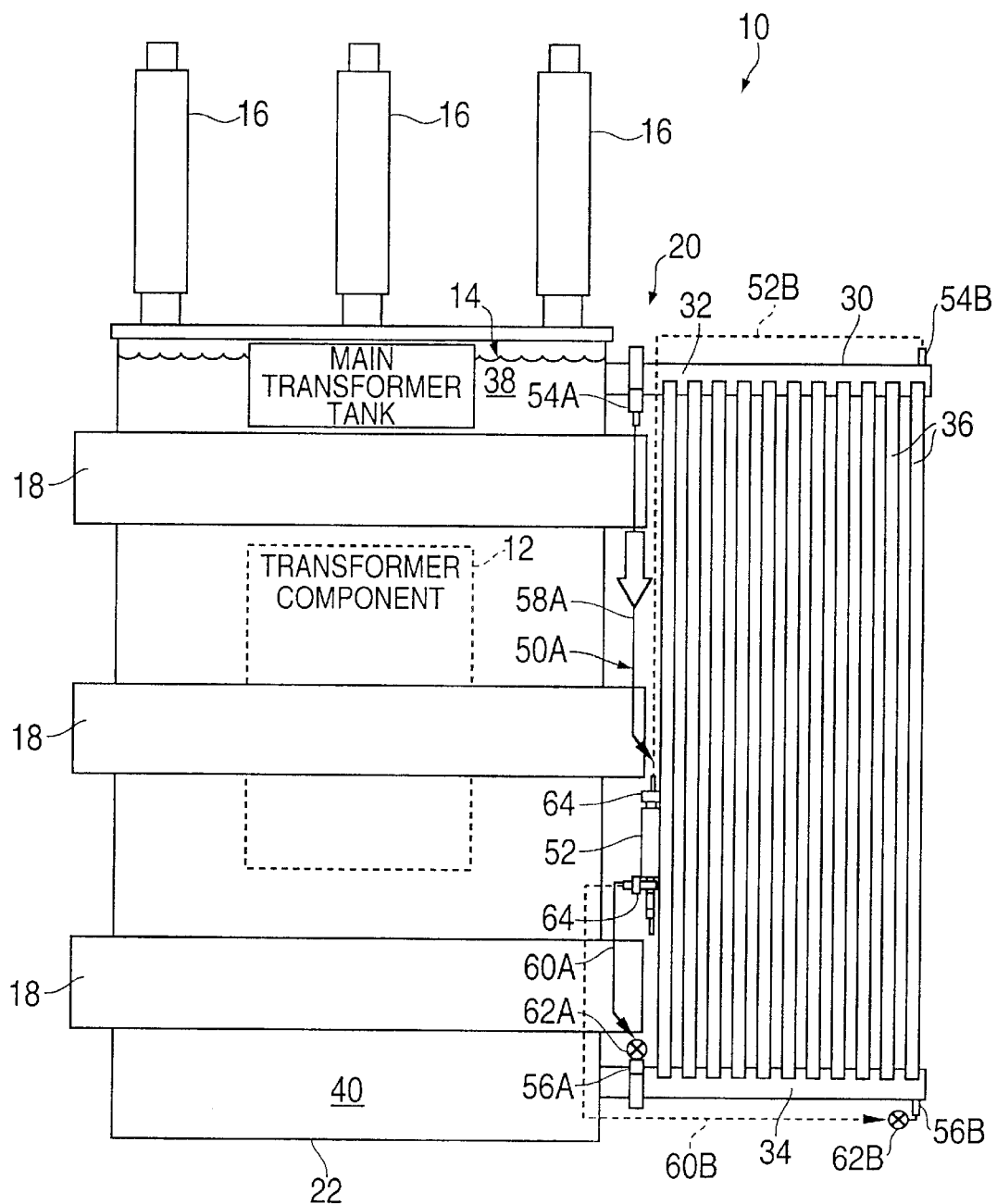
FIG. 1 is a front view of a power transformer with an oil sampling system of the present invention.

Referring to FIGS. 1 and 2, a power transformer 10 and an oil containing apparatus 20 are shown with a number of different embodiments of an oil sampling system 50 of the present invention. Oil containing apparatus 20 includes a tank 22 and a radiator 30. A volume of oil 14 is contained in tank 22 and radiator 30. Transformer 10 has a component, such as a winding and a core that are submerged in oil 14 in tank 22. Power transformer 10 also has a plurality of bushings 16. Tank 22 has a top fill valve 24 and a bottom drain valve 26. A plurality of stiffeners 18 provide support and strength for tank 22.

Radiator 30 includes a top header pipe 32, a bottom header pipe 34 and a plurality of fins 36 connected there between. Oil 14 heated by transformer component 12 is cooled by radiator 30. Heated oil 14 flows from an upper region 38 of tank 22 through header pipe 32, fins 36 and bottom header pipe 34 to a bottom region 40 of tank 22.

Oil sampling system 50 of the present invention includes an oil sampling device 52 that is connected in a closed loop with oil containing apparatus 20 via an upper port located near the top thereof and a lower port located near the bottom thereof. Three distinct embodiments of oil sampling system 50 are shown in FIGS. 1 and 2, distinguished by the reference suffixes A, B and C.

Referring to FIG. 1, a first embodiment of oil sampling system 50 includes oil sampling device 52, an upper port 54A, a lower port 56A and oil conduits 58A and 60A. Upper port 54A is connected to top header pipe 32 and lower port 56A is connected to bottom header pipe 34. Conduit 58A connects one end of oil sampling device 52 to upper port 54A and conduit 60A connects the other end of oil sampling device 52 to lower port 56A via a check valve 62A. Dry break connectors 64 permit oil sampling device 52 to be quickly connected and disconnected to conduits 58 and 60. As heated oil 14 cools, its density increases with a resultant downward flow aided by gravity in the closed loop formed by upper and lower ports 54A and 56A of oil containing apparatus 20, conduits 58A and 60A and oil sampling device 52. After connection in the loop, oil flow through sampling device 52 quickly becomes bubble free. Sampling device 52 can then be removed for analysis. With oil sampling system 50, there is no need for a flush container or a flush operation.

Still referring to FIG. 1, an alternative embodiment of oil sampling system 50 includes an upper port 54B and a lower port 56B. Upper port 54B is disposed at another location along top header pipe 32. Upper port 54B is connected to oil sampling device 52 by way of a conduit 52B. Lower port 56B is connected to oil sampling device 52 via a conduit 60B and a check valve 62B.

Referring to FIG. 2, another alternative embodiment of oil sampling system 50 has an upper port 54C connected with top fill valve 24 and a lower port 56C connected with bottom drain valve 26. Upper port 54C is connected to oil sampling device 52 by way of a conduit 58C. Lower port 56C is connected to oil sampling device 52 via a conduit 60C and a check valve 62C. It will be apparent to those skilled in the art that the A embodiment could use either lower port 56B or 56C instead of lower port 56A, that the B embodiment could use either lower port 56A or 56C instead of lower port 56B and that the C embodiment could use either lower port 56A or 56B.

Check valves 62A, 62B and 62C prevent a back flow of oil from lower ports 56A, 56B and 56C as might occur, for example, by a leak in the supply tubing or the supply itself, or by an unintended disconnect in the system. In such case, the check valves prevent undesirable loss of oil from the oil tank.

The method of the invention starts with connecting oil sampling device 52 in a closed loop, for example the closed loop of the A embodiment, with oil containing apparatus 20. This is readily achieved by field service personnel by means of dry break connectors 64. Then oil is passed through oil sampling device 52 for a period of time to assure that the oil is bubble free. Oil sampling device 52 is then disconnected for analysis. An important variation of the method is that after the time of removal for analysis, another oil sampling device is installed so that it will already be in place when it is later desired to obtain another sample.

Figure 3:
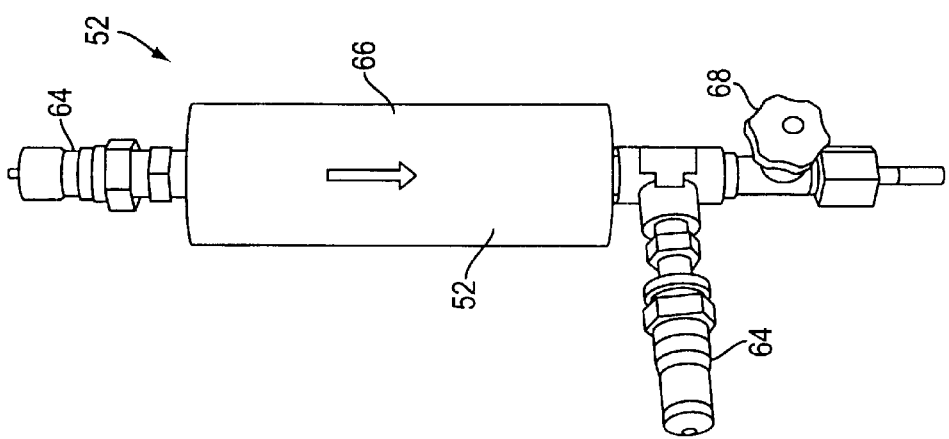
FIG. 3 is a perspective view of an oil sampling device of the oil sampling system of FIG. 1.

Referring to FIG. 3, oil sampling device 52 includes a sample container 66 that is mounted between dry break connectors 64. A valve 68 is provided to remove the oil sample from sample container 66 for analysis.

Figure 4:
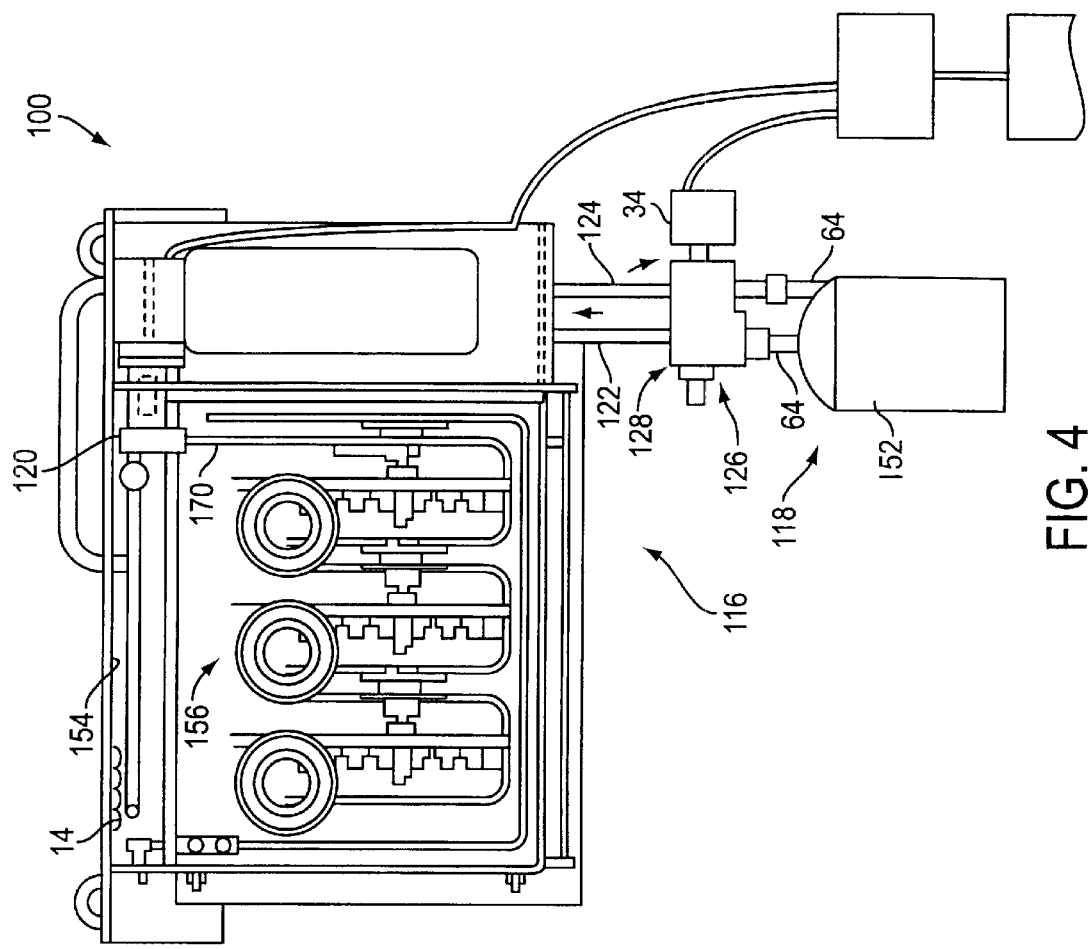
FIG. 4 is a schematic diagram of a load tap changer with an oil sampling system of the present invention.

Referring to FIG. 4, a load tap changer 100 and an oil containing apparatus 116 are shown with an oil sampling system 118 of the present invention. Oil containing apparatus 116 includes a tank 154 that is filled with oil 14 and a filter assembly 126. A mechanism 156 of load tap changer 100 is immersed in oil 14 in tank 154. Pump 120 is operable to pump oil via a pick up tube 170 from close to the bottom of tank 154. The pumped oil is circulated in a closed loop via an outlet conduit 124, a manifold 128 of filter assembly 126 to oil sampling device 152 and returned to an upper region of tank 154 via an inlet conduit 122. To obtain an oil sample, oil sampling device 152 is connected to manifold 128 via dry break connectors 64. Oil is pumped through the closed loop. When the pumped oil is bubble free, oil sampling device 152 is disconnected for analysis.

Figure 5:
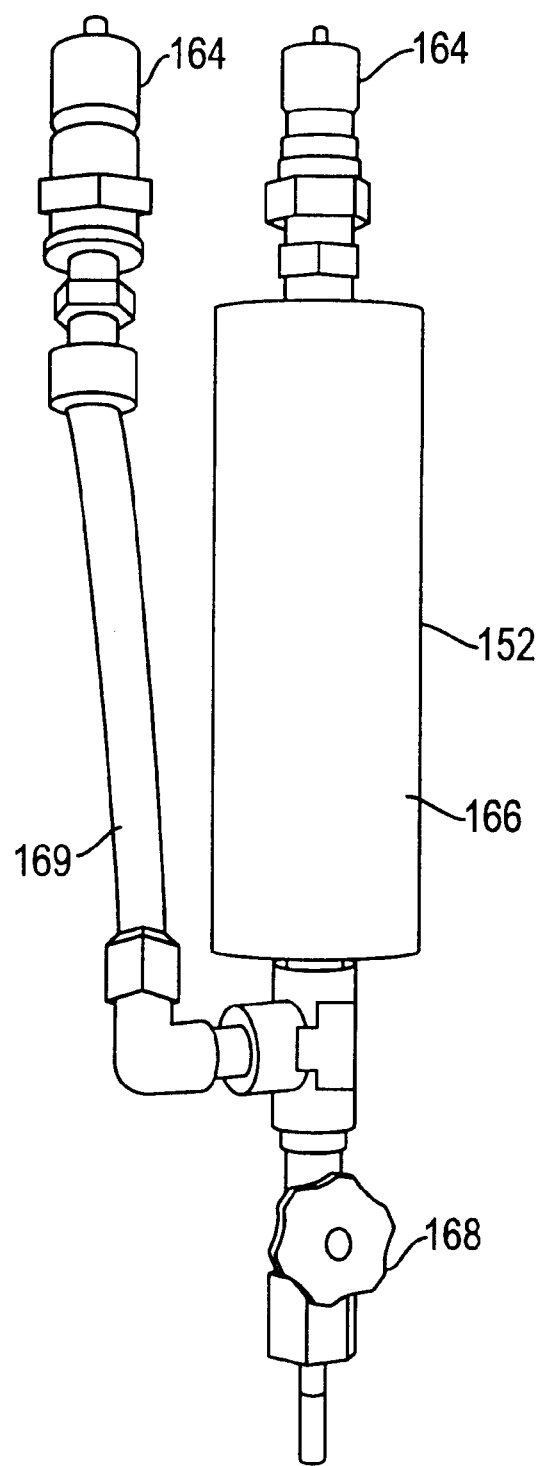
FIG. 5 is a perspective view of the oil sampling device of FIG. 4.

Though not shown in FIG. 4, filter assembly 126 also has a filter canister that is connected via dry break connectors 64 to manifold 126 for normal operation when a sample is not being taken. To take a sample, the filter canister is replaced by oil sampling device 152. FIG. 5 illustrates the oil sampling device 152 including a sample container 166 that is disposed between dry break connectors 164. A valve 168 is provided to remove the oil sample for analysis. In this embodiment a hose 169 is provided to provide flexible movement of the connectors 164 to facilitate attachment and release of the connector 164. If a flexible hose 169 is not employed it can be difficult to line up and attach the connectors 164.

The present invention having been thus described with particular reference to the preferred forms thereof, it will be obvious that various changes and modifications may be made therein without departing from the spirit and scope of the present invention as defined in the appended claims.

The invention claimed is:

1. An oil sampling system for an electrical power device, comprising:

an oil containing apparatus that contains a volume of oil and that includes a tank in which a component of said electrical power device is submerged in said oil;

first and second ports connected to said oil containing apparatus;

a sampling device that is positioned external to said tank and between and upper region of said tank and a bottom region of said tank; and connectors for removably connecting said sampling device between said first and second ports so that said oil flows through said sampling device in a closed loop with said oil containing apparatus, wherein said first port is located to receive a flow of said oil from an active region of said oil containing apparatus, wherein said first and second ports are vertically displaced from one another, wherein said oil flows through said sampling device aided by cooling of said oil and gravity, wherein said oil containing apparatus further includes a radiator connected to said tank, and wherein at least one of said first and second ports is connected to said radiator, wherein said radiator includes a top header pipe and a bottom header pipe, and wherein said first and second ports are connected to said top header pipe and said bottom header pipe, respectively.

2. The oil sampling system of claim 1, wherein said electrical power device is a transformer.

3. The oil sampling system of claim 1, wherein said first port is connected to a top fill valve of said tank.

4. The oil sampling system of claim 1, wherein said second port is connected to a bottom drain valve of said tank.

5. The oil sampling system of claim 1, wherein said oil containing apparatus further comprises a pump that circulates said oil through said closed loop.

6. The oil sampling system of claim 5, wherein said pump pumps said oil from a bottom region of said tank, and wherein said oil flows through said sampling device to an upper region of said tank.

7. The oil sampling system of claim 1, wherein said connectors are dry break connectors.

8. The oil sampling system of claim 1, wherein said electrical power device is a load tap changer.

9. A method of sampling oil from an oil containing apparatus having a tank in which a component of an electrical power device is submerged in oil, said method comprising: (a) connecting a sampling device, which is positioned external to said tank and between an upper region of said tank and a bottom region of said tank, and in a closed loop with first and second ports connected to said oil containing apparatus; (b) passing said oil through said sampling device in said closed loop; and (c) disconnecting said sampling device with a quantity of oil therein as a sample.

10. The method of claim 9 wherein step (a) connects said sampling device to said oil containing apparatus at a location to receive oil from an active region of said oil containing apparatus.

11. The method of claim 10, wherein step (b) passes said oil through said sampling device aided by cooling and gravity.

12. The method of claim 11, wherein said oil containing apparatus has first and second vertically displaced ports, and wherein step (a) connects said sampling device between said first and second ports.

13. The method of claim 12, wherein said oil containing apparatus further includes a radiator that cools said oil, and wherein at least one of said ports is attached to said radiator.

14. The method of claim 13, wherein said radiator includes a top header pipe and a bottom header pipe, and wherein said first and second ports are connected to said top header pipe and said bottom header pipe, respectively.

15. The method of claim 9, further comprising (d) after step (c), connecting another sampling device in said closed loop, and thereafter repeating steps (b), (c) and (d).

16. The method of claim 9, wherein step (b) pumps said oil through said sampling device in said closed loop.

17. The method of claim 16, wherein step (b) pumps said oil from a bottom region of said tank and returns said oil to an upper region of said tank.

18. An oil sampling system for an electrical power device, comprising:
an oil containing apparatus that contains a volume of oil and that includes a tank in which a component of said electrical power device is submerged in said oil;
a radiator coupled to said tank having a top header pipe and a bottom header pipe;
a sampling device that is positioned external to said radiator between the top header pipe and the bottom header pipe; and
connectors for removeably connecting said sampling device between the top header pipe and the bottom header pipe so that oil flows through said sampling device in a closed loop with said oil containing apparatus.

19. The oil sampling system of claim 18, wherein said connectors comprises a first connector and positioned at a port first and a second connector positioned at a second port, respectively, wherein said first port is located to receive a flow of said oil from an active region of said oil containing apparatus, and wherein said first port and said second port are vertically displaced from one another.

20. The oil sampling system of claim 19, wherein said first port is connected to a top fill valve of said tank, and wherein said second port is connected to a bottom drain valve of said tank.

21. The oil sampling system of claim 19, wherein said oil containing apparatus further includes a radiator connected to said tank, and wherein at least one of said first port and said second port is connected to said radiator.

22. The oil sampling system of claim 18, wherein said electrical power device is a transformer.

23. The oil sampling t of claim 18, wherein said connectors are dry break connectors.

24. An oil sampling system for an electrical power device, comprising:
an oil containing apparatus that contains a volume of oil and that includes a tank in which a component of said electrical power device is submerged in said oil;
a top valve positioned at the top of the tank and a bottom valve positioned at the bottom of the tank;
first and second ports connected to said oil containing apparatus;
a sampling device that is positioned external to said tank between the top valve of the tank and the bottom valve of the tank; and
connectors for removeably connecting said sampling device between said first and second ports so that oil flows through said sampling device in a closed loop with said oil containing apparatus.

25. The oil sampling system of claim 24, wherein said radiator include a top header pipe and a bottom header pipe, and wherein said first port is connected to said top header pipe and said port is connected to said bottom header pipe.

26. The oil sampling system of claim 24, wherein said connectors are dry break connectors.

27. An oil sampling system for an electrical power device, comprising:
an oil containing apparatus that contains a volume of oil and that includes a tank in which a component of said electrical power device is submerged in said oil;
a radiator coupled to said tank;
first and second ports connected to said oil containing apparatus;
a sampling device that is positioned external to said radiator between a top of the radiator and a bottom of the radiator; and
connectors for removably connecting said sampling device between said first and second ports so that said oil flows through said sampling device in a closed loop with said oil containing apparatus.

* * * * *